United States Patent

Jisai et al.

Patent Number: 5,183,601
Date of Patent: Feb. 2, 1993

[54] DETERGENT COMPOSITION CONTAINING POLYETHYLENIMINE CO-POLYMER

[75] Inventors: Yasuhiro Jisai; Yukiomi Tanaka, both of Chiba; Akira Shigeta, Tokyo, Japan

[73] Assignee: Kao Corporation, Tokyo, Japan

[21] Appl. No.: 706,210

[22] Filed: May 28, 1991

[30] Foreign Application Priority Data

Jun. 7, 1990 [JP] Japan .................. 2-149192
Jun. 7, 1990 [JP] Japan .................. 2-149193
Jun. 7, 1990 [JP] Japan .................. 2-149195
Jun. 7, 1990 [JP] Japan .................. 2-149196
Jun. 7, 1990 [JP] Japan .................. 2-149198

[51] Int. Cl.$^5$ .................. C11D 3/28; C11D 1/02; C11D 1/66; C11D 1/90
[52] U.S. Cl. .................. 252/524; 252/544; 252/525; 252/174.23; 252/DIG. 2; 424/70
[58] Field of Search .......... 252/544, 525, 524, 174.23, 252/DIG. 2; 424/70

[56] References Cited

U.S. PATENT DOCUMENTS 4,902,499 2/1990 Bolish, Jr. et al. ......... 252/DIG. 13

FOREIGN PATENT DOCUMENTS 59-230027 12/1984 Japan .................. 252/174.23

*Primary Examiner*—Paul Lieberman
*Assistant Examiner*—Kery A. Fries
*Attorney, Agent, or Firm*—Oblon, Spivak, McClelland, Maier & Neustadt

[57] ABSTRACT

A detergent composition comprising: (1) a surface active agent or a water-soluble polymeric compound and (2) a polymer which contains recurring units (I-1) and (I-2).

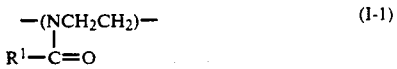

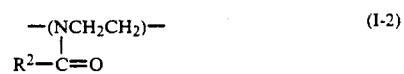

wherein $R^1$ is a hydrogen or a methyl or ethyl group, $R^2$ represents an alkyl, aryl or aralkyl group having 4–15 carbon atoms. The detergent composition exhibits extremely reduced irritation to the skin and the hair, possesses outstanding detergency and foaming and foam-breaking capability, and imparts an excellent feeling upon use.

16 Claims, No Drawings

DETERGENT COMPOSITION CONTAINING POLYETHYLENIMINE CO-POLYMER

BACKGROUND OF THE INVENTION

1. Field of the Invention

The present invention relates to a novel detergent composition, and, more particularly, to a detergent composition exhibiting extremely reduced irritation to the skin and the hair, possessing outstanding detergency and foaming and foam-breaking capability, and imparting an excellent feeling upon use.

2. Description of the Background Art

Anionic, cationic, amphoteric, and nonionic surface active agents have conventionally been used for detergent compositions for washing the skin, the hair, and the like.

Although anionic surface active agents possess good detergency and foaming capability, their irritation to the skin and the hair is sometimes problem. Nonionic surface active agents are inferior to other surface active agents in their foaming capability and in the quality of the foam. For example, polyoxyethylenealkyl ether has a low foaming capability. Alkylpolyglycosides do not produce foam swiftly and the foam produced is rough in quality. Amphoteric surface active agents have good foaming capability, but the foam is rough in quality, exhibiting only insufficient detergency toward sebum and fats. They impart an inadequate feeling after washing. Detergent compositions containing cationic surface active agents have drawbacks in their poor foaming capability, bad quality of the foam, and unpleasant feelings which they impart after rinsing. Furthermore, they sometimes impart irritation to the skin depending upon the manner and the conditions under which they are used.

In view of this situation, the present inventors have undertaken extensive studies in order to develop a detergent composition which is free from the drawbacks which each type of surface active agent have. As a result, the present inventors have found that a detergent composition exhibiting extremely reduced irritation to the skin and the hair, possessing excellent detergency and foaming and foam-breaking capability, and imparting an excellent feeling upon use could be produced by using these surface active agents together with a specific type of polyethylene imine polymeric compound, and further that its detergency and foaming capability could be promoted even more, and the composition provided a minimal degree of irritation and a comfortable massage feeling to the skin and the hair, if a water-soluble polymer is used together with the polyethylene imine polymeric compound. Such findings have led to the completion of the present invention.

SUMMARY OF THE INVENTION

Accordingly, an object of the present invention is to provide a detergent composition comprising:

(A) a polymeric compound comprising recurring units (I-1) and (I-2) at a ratio by weight of 9:1–1:9, $$-(NCH_2CH_2)- \atop R^1-C=O \qquad \text{(I-1)}$$

wherein $R^1$ is a hydrogen or a methyl or ethyl group, $R^2$ represents an alkyl, aryl or aralkyl group having 4–15 carbon atoms, and (B) at least one member selected from surface active agents and water-soluble polymer.

Other objects, features and advantages of the invention will hereinafter become more readily apparent from the following description.

DETAILED DESCRIPTION OF THE INVENTION AND PREFERRED EMBODIMENTS

Butyl, pentyl, hexyl, heptyl, octyl, nonyl, decyl, undecyl, tridecyl, pentadecyl, 2-methylpentyl, 2-propylheptyl, phenyl, p-methylphenyl, p-ethylphenyl, benzyl, naphtyl groups are given as examples of the group $R^2$ in the recurring unit of formula (I-2) which constitutes the polymeric compound of component (A). Especially preferable groups are those having 6–12 carbon atoms.

The N-terminal of polymeric compound (A) may be methyl, ethyl, propyl, dodecyl, or the like, with an especially preferable N-terminal group being methyl or ethyl. The C-terminal of polymeric compound (A) may be hydroxyl, acetyl, laurylamine, diethanolamine, or the like. For the compound used in the present invention, hydroxyl and acetyl groups are most preferable. Although there are no restrictions as to the molecular weight of the polymeric compound (A), its preferable molecular weight range is 500–20,000, especially 1,000–6,000.

The structure of the copolymer may be either block or random, with the preferred structure being the block copolymer. In the combination of recurring units (I-1) and (I-2), either one type of unit from (I-1) and from (I-2) may constitute a combination or two or more types from (I-1) and from (I-2) may be combined. A preferred combination of units (I-1) and (I-2) is that having the carbon atom content of $R^1$ in (I-1) and that of $R^2$ in (I-2) different 3 or more from each other. The ratio by weight of the recurring units (I-1) and (I-2) in the copolymer is 9:1–1:9, and particularly preferably 9:1–4:6.

The synthesis of polymer (A) used in the present invention can be carried out, for example, by the cationic polymerization involving ring-opening and isomerization of 2-substituted-2-oxazoline, e.g. 2-ethyl-2-oxazoline, in accordance with Polym. J. 4, 87 (1973). For the preparation of the block copolymer, two or more types of 2-oxazoline monomers are successively polymerized by the ring-opening according, for example, to the description in Japanese Patent Laid-open (kokai) No. 230027/1984. The random polymerization is performed by mixing two or more types of 2-oxazoline monomers and effecting ring-opening at one time.

The amount of polymer (A) in the detergent composition of the present invention is depending on the types of the products. For example, the amount may be 1–40% by weight for the liquid detergent composition, 10–70% by weight for the gel type detergent composition, and 20–80% by weight for the solid detergent composition.

Component (B) of the detergent composition of the present invention includes anionic, cationic, amphoteric, and nonionic surface active agents. Of these, preferred anionic surface active agents (hereinafter referred to from time to time as component (B)-1) from the aspect of foaming capability are fatty acid, alkylsulfate, alkyl ether carboxylate, polyoxyethylenealkyl ether sulfate, phosphate, N-acylamino acid, isethionate, and sulfo-succinate compounds. Either one kind or a combination of two or more kinds of these anionic surface active agents can be used in the present invention. Phosphate, isethionate and sulfosuccinate compounds are less irritative and thus are particularly preferable.

Preferred fatty acid and alkylsulfate anionic surface active agents are those having a linear or branched, saturated or unsaturated alkyl group of a 8-20 carbon atom content and having an alkali metal or alkanol amine as a counter ion.

Preferred alkyl ether carboxylate and polyoxyethylenealkyl ether sulfate anionic surface active agents are those having the same type of alkyl group counter ion as defined for the fatty acid and alkylsulfate anionic surface active agents and, in addition, containing 1-50 moles of ethylene oxide in average.

Given as examples of preferred phosphate type anionic surface active agents are those having the following formula (II) or (III).

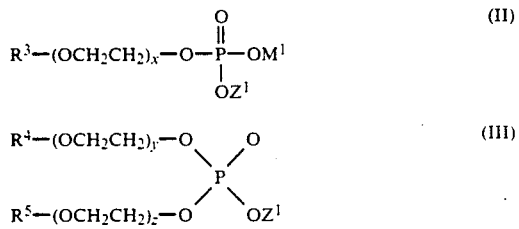

wherein $R^3$, $R^4$, and $R^5$ individually represent a linear or branched alkyl or alkenyl group of a 8-18 carbon atom content. $Z^1$ and $M^1$ individually represent a hydrogen, an alkali metal, or an alkanol amine having a hydroxyalkyl group of a 2-3 carbon atom content, and x, y and z are a number of 0-10. Particularly preferable compounds represented by formula (II) or (III) are those containing 0-3 moles of ethylene oxide, especially containing no ethylene oxide, and having an alkyl group of a 12-14 carbon atom content. Specific examples include sodium mono- or dilauryl phosphate, potassium mono- or dilauryl phosphate, mono- or dilauryl diethanolamine, mono- or dilauryl triethanolamine, sodium mono- or dimyristyl phosphate, potassium mono- or dimyristyl phosphate, mono- or dimyristyl phosphate diethanolamine, mono- or dimyristyl phosphate triethanolamine, and the like.

When the compounds of formulae (II) and (III) are used together as anionic surface active agents, a preferable ratio of compound (II) and compound (III) is 10:0-5:5, especially preferably 10:0-7:3.

Given as examples of N-acylamino acid type anionic surface active agents are compounds of the following formula (IV).

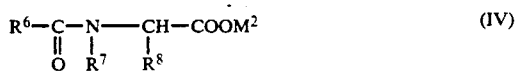

wherein $R^6$ represents a linear or branched alkyl or alkenyl group of a 7-21 carbon atom content, $R^7$ represents a hydrogen atom, an alkyl or alkenyl group of a 1-4 carbon atom content, $R^8$ is a group represented by formula $-(CH_2)_pR^9$ (wherein p is an integer of 0-4 and $R^9$ is a hydrogen, a hydroxyl group, or a group $COOM^2$), and $M^2$ represents a hydrogen, an alkali metal, or an alkanol amine.

There are the L-isomer, D-isomer and lacemate for the compound represented by formula (IV), all of which can be used for the purpose of the present invention. Preferable compounds of formula (IV) are N-myristylglutamic acid, N-laurylglutamic acid, N-lauroyl-N-methylglycine, N-lauroylaspartic acid, N-lauroyl serine, and the like, as well as their alkali metal salts and alkanol amine salts.

Typical examples of isethionate type anionic surface active agents are compounds of the following formula (V).

wherein $R^{10}$ represents an alkyl or alkenyl group of a 7-21 carbon atom content and $M^3$ represents a hydrogen, an alkali metal, or an alkanol amine.

Lauric acid group, myristic acid group, oleic acid group, coconut oil fatty acid group, and the like are given as examples of fatty acid group represented by $R^{10}-COO-$. Counter cations represented by $M^3$ include sodium, potassium, triethanolamine, diethanolamine, monoethanolamine, and the like.

Examples given for sulfo-succinic acid type anionic surface active agents are esters of a higher alcohol or its ethoxylate and sulfo-succinic acid, or sulfo-succinic acid esters derived from a higher fatty acid amide, which are represented by the following formulae (VI) and (VII).

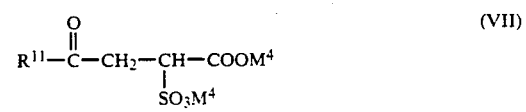

wherein $R^{11}$ represents a group $R^{12}O-(CH_2CH_2O)_q-$ or $R^{13}CONH-(CH_2CH_2O)_q-$ (wherein $R^{12}$ represents a linear or branched alkyl or alkenyl group of a 8-22 carbon atom content, $R^{13}$ represents a linear or branched alkyl or alkenyl group of a 7-21 carbon atom content, and q is a number of 0-20) and $M^4$ is a hydrogen or a cation forming a water-soluble salt and selected from the group consisting of alkali metal ion, alkaline earth metal ion, ammonium ion, and organic ammonium ion.

Of the esters of a higher alcohol or its ethoxylate and sulfo-succinic acid represented by formula (VI) or (VII), preferable compounds are disodium salts of secondary alcohol ($C_{11-13}$) ethoxylate sulfo-succinate (e.g. Softanol MES-3, 5, 7, 9, 12; EO=3, 5, 7, 9, and 12 moles, respectively: trademarks of Nippon Shokubai Kagaku Kogyo Co.), disodium salts of lauryl alcohol or its ethoxylate (EO=3, 6, 9, or 12) sulfo-succinate, disodium salts of ester of synthetic primary alcohol ($C_{12-15}$) or its ethoxylate (EO=2-4) and sulfo-succinic acid, and the like. Typical examples of sulfo-succinic acid esters derived from a higher fatty acid amide represented by formula (VI) or (VII) include disodium salts of lauric acid polyethylene glycol (EO=1 or 2) amide and sulfo-succinate, disodium salts of oleic acid polyethylene glycol (EO=1 or 2) amide sulfo-succinate, sodium salt of coconut oil fatty acid-polyethylene glycol (EO=4) and sulfo-succinate, and the like.

The amount of anionic surface active agents (component (B)-1) to be incorporated in the detergent composition of the present invention is dependent on the types of the products. A suitable amount, for example, may be 1-30% by weight for the liquid detergent composition, 10-50% by weight for the gel type detergent composition, and 20-80% by weight for the solid detergent composition. A preferable ratio of component (A) and component (B)-1 is 10:1-1:100, and especially preferably 5:1-1:5.

The detergent composition in which component (A) and component (B)-1 are incorporated exhibits excellent detergency, foaming capability, and foam-breaking capability, imparts an excellent feeling upon use, and gives extremely reduced irritation to the skin and the hair.

Nonionic surface active agents which can be used as component (B) (hereinafter referred to from time to time as component (B)-2) include, for example, polyoxyalkylene type nonionic surface active agents such as polyoxyethylene alkyl ether, polyoxypropylene alkyl ether, polyoxyethylene alkylphenyl ether, polyoxyethylene glycol fatty acid ester, ethylene oxide derivative of propylene glycol fatty acid ester, polyoxyethylene sorbitane fatty acid ester, ethylene oxide derivative of mono- or polyglycerine fatty acid ester, ethylene oxide derivative of trimethylolpropane fatty acid ester, polyoxyethylene hydrogenated castor oil, polyoxyethylene hydrogenated castor oil fatty acid ester, polyoxyethylene hydrogenated castor oil pyroglutamic acid ester, polyoxyethylene glyceryl pyroglutamic acid ester, and the like; saccharide ester type surface active agents; saccharide ether type surface active agents; saccharide amide type surface active agents; polyglycerine fatty acid esters; polyglycerine alkyl ethers; alkylamine oxides; and the like.

Of the above nonionic surface active agents of component (B)-2, those having an HLB value of greater than 4, particularly of 6-16, are preferable. The HLB value here is the value determined from the inorganic and organic values proposed by Oda, Terajima, et al. according to the following equation.

$$HLB = \frac{\Sigma \text{ inorganic value}}{\Sigma \text{ organic value}} \times 10$$

Typical saccharide ester type surface active agents are sucrose fatty acid ester surface active agents. Examples of typical saccharide ether type surface active agents are alkyl glycoside type surface active agents represented by the following formula (VII).

$$R^{14}-O-(R^{15}O)_m-G_n \quad \text{(VII)}$$

wherein $R^{14}$ represents a linear or branched alkyl, alkenyl, or alkylphenyl group having 6-18 carbon atoms, $R^{15}$ represents an alkylene group having 2-4 carbon atoms, G is a reducing sugar having 5-6 carbon atoms, m denotes a value of 0-10, and n denotes a value of 1-10. Of these, particularly preferable are decylglycoside, laurylglycoside, laurylpolyglycoside, decylpolyglycoside, and the like. Specific saccharide amide surface active agents include compounds represented by the following formula (VIII)

wherein $R^{16}$ represents a linear or branched alkyl, alkenyl, or alkylphenyl group having 5-17 carbon atoms, $R^{17}$ represents a hydrogen atom, a linear or branched alkyl or alkenyl group having 1-18 carbon atoms, a group

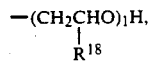

wherein $R^{18}$ represents a hydrogen atom or methyl group and l denotes a value of 0-30, or a group $-CH_2-CH_2-OH$,

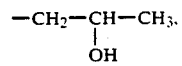

or $-CH_2-CH_2-CH_2-OH$, and $Z^2$ represents a polyhydroxyalkyl group derived from saccharide residue having 4-30 carbon atoms.

Enumerated as specific examples of polyoxyalkylene type nonionic surface active agents are polyoxyethylene(5) hydrogenated castor oil, polyoxyethylene(7) hydrogenated castor oil, polyoxyethylene(10) hydrogenated castor oil, polyoxyethylene(20) hydrogenated castor oil, polyoxyethylene(30) hydrogenated castor oil, polyoxyethylene(40) hydrogenated castor oil, polyoxyethylene(50) hydrogenated castor oil, polyoxyethylene(60) hydrogenated castor oil, polyoxyethylene(3) lauryl ether, polyoxyethylene(5) stearyl ether, polyoxyethylene(5) decyltetradecyl ether, polyoxyethylene(10) decyltetradecyl ether, polyoxyethylene(5) hexyldecyl ether, polyoxyethylene(5) octyldodecyl ether, polyoxyethylene(15) decyltetradecyl ether, polyoxyethylene(20) decyltetradecyl ether, polyoxyethylene(25) decyltetradecyl ether, polyoxyethylene(10) hexyldecyl ether, polyoxyethylene(15) hexyldecyl ether, polyoxyethylene(20) hexyldecyl ether, polyoxyethylene(25) hexyldecyl ether, polyoxyethylene(10) octyldodecyl ether, polyoxyethylene(16) octyldodecyl ether, polyoxyethylene(20) octyldodecyl ether, polyoxyethylene(25) octyldodecyl ether, polyoxyethylene(3) glyceryl monoisostearate, polyoxyethylene(6) glyceryl monoisostearate, polyoxyethylene(10) glyceryl triisostearate, polyoxyethylene(20) glyceryl triisostearate, polyoxyethylene(8) trimethylolpropane trimyristate, polyoxyethylene(20) trimethylolpropane trimyristate, polyoxyethylene(6) diisostearate, polyoxyethylene(12) diisostearate, polyoxyethylene(5) cetyl ether stearate, polyoxyethylene(10) cetyl ether stearate, polyoxyethylene(15) glyceryl monoisostearate, polyoxyethylene(30) glyceryl monoisostearate, polyoxyethylene(30) glyceryl triisostearate, polyoxyethylene(40) glyceryl triisostearate, polyoxyethylene(30) trimethylolpropane myristate, polyoxyethylene(6) sorbitane monolaurate, polyoxyethylene(20) sorbitane monolaurate, polyoxyethylene(20) sorbitane monostearate, polyoxyethylene(20) sorbitane monooleate, polyoxyethylene(30) sorbitol tetraoleate, polyoxyethylene(40) sorbitol tetraoleate, and the like. Of these, particularly preferable compounds are polyoxyethylene alkyl ether, polyoxyethylene sorbitane fatty acid ester, polyoxyethylene hydrogenated castor oil, and the like. These are used individually or in combination of two or more.

The amount of component (B)-2 to be incorporated in the detergent composition of the present invention is dependent on the types of the products. A suitable amount, for example, may be 1-50% by weight for the liquid detergent composition, 5-80% by weight for the gel type detergent composition, and 10-80% by weight for the solid detergent composition. The preferable ratio of component (A) and component (B)-2 is 10:1-1:100, and especially preferably 5:1-1:5.

The detergent composition in which component (A) and component (B)-2 are incorporated overcomes the inferior foaming capability and inadequate quality of the foam which are drawbacks of nonionic surface active agents, and exhibits improved detergency, providing reduced irritation to the skin and the hair.

Amphoteric surface active agents which can be used as component (B) (hereinafter referred to from time to time as component (B)-3) include (1) amidoamine type surface active agents, (2) amino acid type surface active agents, (3) betaine type surface active agents, (4) sulfate type surface active agents, (5) sulfonate type surface active agents, (6) phosphate type surface active agents, and (7) amine oxide type surface active agents, and the like.

Examples given for amidoamine type surface active agents as component (B)-3 in the present invention are compounds represented by formula (IX) or (X):

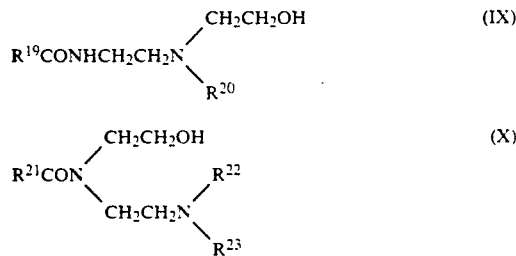

wherein $R^{19}$ and $R^{21}$ each independently represent a saturated or unsaturated hydrocarbon group having 7 to 19 carbon atoms, $R^{20}$ and $R^{22}$ each independently represent a group $-CH_2COOM^2 \geq CH_2CH_2COOM^2$ or

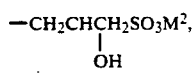

wherein $M^2$ stands for a hydrogen atom, an alkali metal, or an alkanol amine, $R^{23}$ represents a hydrogen atom, a group $-CH_2COOM^2$, $-CH_2CH_2COOM^2$, or

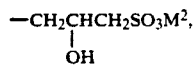

wherein $M^2$ has the same meaning as defined above.

Compounds represented by formula (XI) and (XII) are examples of amino acid type surface active agents used as component (B)-3 in the present invention.

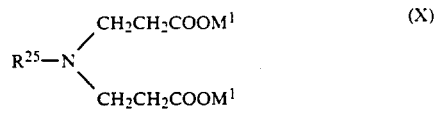

wherein $R^{24}$ and $R^{25}$ each independently represent an alkyl, alkenyl, aryl, aralkyl, alkylaryl, or alkenylaryl group having 8-24 carbon atoms, $M^1$ is a hydrogen, alkali metal, ammonium ion, or an alkanolamine having a hydroxyalkyl group of a 2-3 carbon atom content, and a is a number 1-4. Particularly preferable compounds represented by (XI) or (XII) are laurylamino propionic acid and myristylamino propionic acid.

Examples given for betaine type surface active agents used as component (B)-3 in the present invention are hydroxysulfo-betaine type, trialkylamino fatty acid betaine type, fatty acid amide dialkylaminoacetic acid betaine type, trialkylaminopropane sulfo betaine type, and imidazoline betaine type compounds represented by formulae (XIII), (XIV), (XV), (XVI), and (XVII).

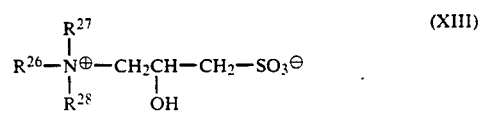

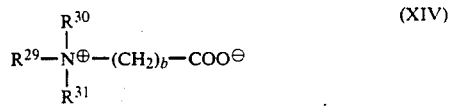

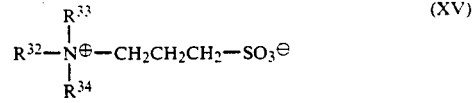

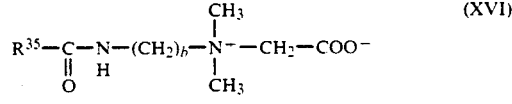

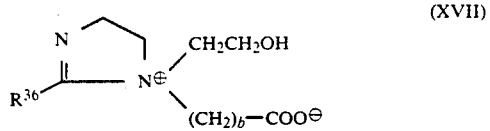

wherein $R^{26}$, $R^{29}$, $R^{32}$, $R^{35}$, and $R^{36}$ are individually a saturated or unsaturated hydrocarbon group having 8-20 carbon atoms, $R^{27}$, $R^{28}$, $R^{30}$, $R^{31}$, $R^{33}$, and $R^{34}$ are individually a lower alkyl group having 1-3 carbon atoms, and b is a number of 1-4. Particularly preferred are compounds those having $R^{26}$, $R^{29}$, and $R^{32}$ which contain 12 carbon atoms and $R^{27}$, $R^{28}$, $R^{30}$, $R^{31}$, $R^{33}$, and $R^{34}$ which is a methyl group.

Sulfate type surface active agents which are given as examples of component (B)-3 usable in the present invention are compounds represented by the following formula (XVIII) of (XIX).

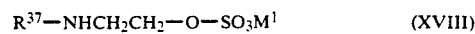

-continued

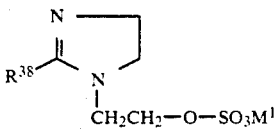
(XIV)

wherein $R^{37}$ and $R^{38}$ are the same as $R^{26}R^{29}$, $R^{32}$, $R^{35}$, and $R^{36}$ and $M^1$ is the same as defined above. Particularly preferred among compounds of formula (XVIII) and (XIX) are those having an acyl group with a 12-18 carbon atom content for $R^{37}$ and sodium for $M^1$ or an alkyl group with a 12-18 carbon atom content for $R^{37}$ and sodium for $M^1$.

Sulfonate type surface active agents which are given as examples of component (B)-3 usable in the present invention are compounds represented by the following formula (XX), (XXI), (XXII), or (XXIII).

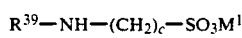
(XX)

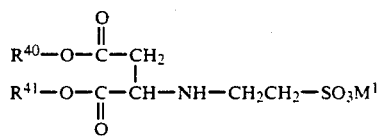
(XXI)

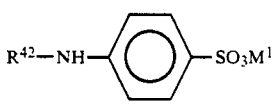
(XXII)

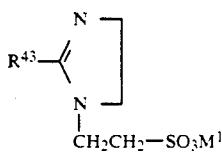
(XXIII)

wherein $R^{39}$, $R^{40}$, $R^{41}$, and $R^{42}$ are the same as $R^{24}$ and $R^{25}$, and $R^{43}$ represents an alkyl, alkenyl, aryl, aralkyl, alkylaryl, alkenylaryl or acyl group having 1-24 carbon atoms, $M^1$ is the same as defined above, and c is a number of 1-4. Preferred compounds of formula (XX), (XXI), (XXII), and (XXIII) are those in which $R^{39}$, $R^{40}$, $R^{41}$, $R^{42}$, or $R^{43}$ is a linear alkyl group having 10-18 carbon atoms. In particular, compounds of formula (XX) in which $R^{39}$ is a linear alkyl group having 10-18 carbon atoms, c is 2, and $M^1$ is sodium; and compounds of formula (XXII) in which $R^{42}$ is a linear alkyl group having 10-18 carbon atoms and $M^1$ is sodium are preferable.

Phosphate type surface active agents which are given as examples of component (B)-3 which can be used in the present invention are compounds represented by the following formula (XXIV).

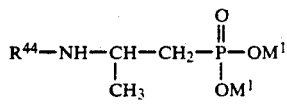
(XXIV)

wherein $R^{44}$ is the same as $R^{24}$ and $R^{25}$ and $M^1$ is the same as defined above. Preferred compounds of formula (XXIV) are those in which $R^{44}$ is a linear alkyl group having 10-18 carbon atoms.

Amine oxide type surface active agents which can be used as component (B)-3 are, for example, compounds represented by the following formula (XXV).

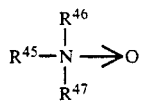
(XXV)

wherein $R^{45}$ is the same as $R^{26}$, $R^{29}$, $R^{32}$, $R^{35}$, and $R^{36}$, and $R^{46}$ and $R^{47}$ are the same as $R^{27}$, $R^{28}$, $R^{30}$, $R^{31}$, $R^{33}$, and $R^{34}$. Preferred compounds of formula (XXV) are those in which $R^{45}$ is a linear alkyl group having 10-18 carbon atoms and $R^{46}$ and $R^{47}$ are methyl or ethyl group.

The amount of component (B)-3 to be incorporated in the detergent composition of the present invention is dependent on the types of the products. A suitable amount, for example, may be 1-50% by weight for the liquid detergent composition, 5-70% by weight for the gel type detergent composition, and 10-90% by weight for the solid detergent composition. The preferable ratio of component (A) and component (B)-3 is 10:1-1:100, and especially preferably 5:1-1:5.

The detergent composition in which component (A) and component (B)-3 are incorporated is mild to the skin owing to their fine foam, exhibits a high detergency, and provides an excellent feeling after use.

Cationic surface active agents which can be used as component (B) (hereinafter referred to from time to time as component (B)-4) include (1) amine salts such as salts of alkylamine, polyamine-fatty acid amide, alkanol amine-fatty acid ester, and the like, (2) polyoxyethylene alkylamines, (3) long chain quaternary ammonium salts, (4) cyclic quaternary ammonium salts, and the like.

Of the amine salts (1), examples which can be given for alkylamine salts are dodecylamine chloride, dioctylamine chloride, and the like; for polyamine-fatty acid amide are the compounds of the following formula (XXVI),

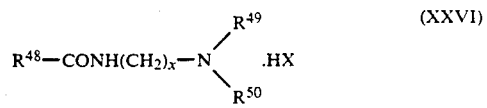
(XXVI)

wherein $R^{48}$, $R^{49}$ and $R^{50}$ are individually a hydrogen or a linear or branched alkyl, alkenyl, or alkylaryl group having 1-30 carbon atoms, x is a number of 0-10, and X is a halogen, alkylsulfate group, or alkylphosphate group; and for alkanol amine-fatty acid ester are the compounds of the following formula (XXVII),

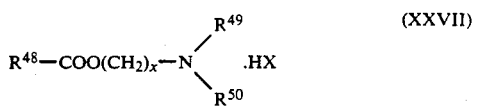
(XXVII)

wherein $R^{48}$, $R^{49}$, $R^{50}$, x and X are the same as defined for formula (XXVI).

Examples given for (2) polyoxyethylene alkylamines are the compounds of the following formula (XXVIII),

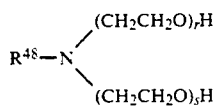

wherein r and s individually indicate a number of 0-100 and $R^{48}$ is the same as defined above.

Examples given for (3) long chain quaternary ammonium salts are the compounds of the following formula (XXIX),

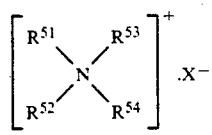

wherein one or two of $R^{51}$, $R^{52}$, $R^{53}$ and $R^{54}$ are a long chain alkyl or hydroxyalkyl group having 8-20 carbon atoms, and the others are an alkyl or hydroxyalkyl having 1-3 carbon atoms, a benzyl group, or a polyoxyethylene group with oxyethylenes of 10 moles or less, and X is the same as defined above. Of the compounds of formula (XXIX), particularly preferable are those represented by formulae (XXX) and (XXXI),

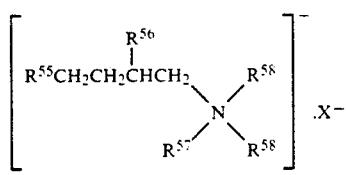

wherein $R^{55}$ and $R^{56}$ individually represent an alkyl group having 10-14 carbon atoms, $R^{57}$ is a group

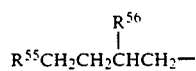

or an alkyl group having 1-3 carbon atoms two $R^{58}$s are independently represent an alkyl or hydroxyalkyl group having 1-3 carbon atoms or a benzyl group, and X is the same as defined above;

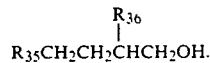

wherein $R^{59}$ is a linear alkyl group having 20-30 carbon atoms, and $R^{58}$ and X are the same as defined above.

Examples given for (3) cyclic quaternary ammonium salts include alkylpyridinium salt, alkylisoquinolinium salt, benzenetonium chloride, and the like.

Among the above cationic surface active agents, particularly preferable compounds are (3) long chain quaternary ammonium salts, and especially those represented by formula (XXX) and (XXXI). The branched long chain quaternary ammonium salts of formulae (XXX) are usually prepared from Guerbet alcohols having 24-32 carbon atoms of formula:

$$R_{35}CH_2CH_2\overset{\overset{R_{36}}{|}}{C}HCH_2OH.$$

Particularly preferable branched quaternary ammonium salts are monoalkyl quaternary ammonium salts such as alkyltrimethyl ammonium salts, alkyldimethylbenzylhydroxyethyl ammonium salts, and alkyldimethylbenzyl ammonium salts; dialkyl quaternary ammonium salts such as dialkyldimethyl ammonium salts, dialkylmethylhydroxyethyl ammonium salts, and dialkylmethylbenzyl ammonium salts; and the like. Counter ions of these ammonium salts may be a halogen ion, e.g. chloride, iodide, bromide; methosulfate, ethosulfate, methophosphate, ethophosphate, or the like. Alkyl groups which are derived from Guerbet alcohol may be 2-decyltetradecyl, 2-dodecylhexadecyl, 2-tetradecyloctadecyl, or the like. Particularly preferable examples of branched quaternary ammonium salts of formula (XXX) are 2-decyltetradecyltrimethyl ammonium chloride, 2-dodecylhexadecyltrimethyl ammonium chloride, 2-tetradecyloctadecyltrimethyl ammonium chloride, and the like.

Mono-linear long chain alkyl quaternary ammonium salts of formula (XXXI) are prepared according to the conventional method. Preferred examples of such quaternary ammonium salts are dodecyltrimethyl ammonium chloride, tetradecyltrimethyl ammonium chloride, hexadecyltrimethyl ammonium chloride, octadecyltrimethyl ammonium chloride, eicosanyltrimethyl ammonium chloride, docosyltrimethyl ammonium chloride, tetracosyltrimethyl ammonium chloride, hexacosyltrimethyl ammonium chloride, octacosyltrimethyl ammonium chloride, triacontanyltrimethyl ammonium chloride, and the like.

The amount of component (B)-4 to be incorporated in the detergent composition of the present invention is not particularly limited. A preferable range is 0.01-80% by weight, with particularly preferable range being 0.1-50% by weight. The preferable ratio of component (A) and component (B)-4 is 10:1-1:100, and especially preferably 5:1-1:5.

The detergent composition in which component (A) and component (B)-4 are incorporated exhibit excellent foaming capability producing foam with good quality and free from unpleasant greasy feeling, reducing the irritation and maintaining the detergency which is inherent to cationic surface active agents.

Water-soluble polymers which can be used as component (B) (hereinafter referred to from time to time as component (B)-5) are not specifically limited so long as the same has a molecular weight of 1,000-10,000,000 and is homogeneously miscible with water. Included are polysaccharides, protein-polyamino acid high molecular compounds, vinyl type high molecular compounds, polyether high molecular compounds, polyamide high molecular compounds, polyester high molecular compounds, polyurethane high molecular compounds, and the like. Of these, typical polysaccharides and their derivatives include naturally occurring polysaccharides or their derivatives such as are guarh-gum, lowcast bean gum, carageenan, gum arabica, tragacanth, pectin, xanthane gum, malmelo extract, dextrin, succinoglucan, hyaluronic acid, chondroitin sulfate, and the like; and synthetic or semi-synthetic polysaccharides or their derivatives such as methyl cellulose, ethyl cellulose, hydroxyethyl cellulose, hydroxypropyl cellulose, carboxymethyl cellulose, cationized cellulose, alginate, propylene glycol alginate, solubilizable starch, carboxymethyl starch, methyl starch, and the like.

Specific examples of protein-polyamino high molecular compounds and their derivatives are gelatin, casein, albumin, cholagen, polyglutamic acid, polylysine, polyalginine, and the like, as well as their derivatives.

Typical vinyl type high molecular compounds and their derivatives are polyvinyl alcohol, polyvinyl ethers (e.g. polyvinyl methyl ether, polyvinyl ethyl ether), acrylic or methacrylic polymers (e.g. polyacrylic acid, hydroxyethyl polyacrylate, dimethylaminoethyl polymethacrylate), polyacrylic or polymethacrylic amides (e.g. polymethacrylic amide, poly-N,N-dimethylacrylic amides), polyvinylpyrrolidone, poly-N-vinylimidazole, poly-4-vinylpyridine, polymers containing carboxyvinyl group (e.g. maleic acid), poly(N,N-dimethyl-3,5-methylenepiperidinium chloride) (Marcoat 100, a product of Merc Co.), N,N-dimethyl-3,5-methylenepiperidinium chloride-acrylamide copolymer (Marcoat 550, a product of Merc Co.), as well as their derivatives and copolymers containing the monomers constituting these polymers.

Other water-soluble high molecular compounds and their derivatives include polyethers (e.g. polyethylene glycol), polyamides (e.g. water-soluble nylon), polyesters, water-soluble polyurethanes, and the like, as well as their derivatives.

Particularly preferable among these water-soluble polymers which are component (B)-5 in the present invention are xanthane gum, acrylic polymers, cationized cellulose, methacrylic acid amphoteric ion polymers (e.g. N-methacryloylethyl-N,N-dimethyl ammonium-α-N-methylacrboxy betaine/butyl methacrylate copolymer, Yukaformer-AM$^{75:}$ trademark, a product of Mitsubishi Petrochemical Co.), carboxymethyl cellulose, polyethylene glycol, as well as their derivatives.

The amount of component (B)-5 to be incorporated in the detergent composition of the present invention is dependent on the types of the products. For example, a preferable amount may be 0.01-10% by weight for the liquid composition, 0.1-30% by weight for the gel type detergent composition, and 1.0-50% by weight for the solid detergent composition. The preferable ratio of component (A) and component (B)-5 is 10:0.1-1:100, and especially preferably 5:0.1-1:5

The detergent composition in which component (A) and component (B)-5 are incorporated has excellent detergency and foaming capability, does not impart unpleasant creaky feeling during washing, providing a pleasant massage feeling, and exhibits an extremely low irritating feeling to the skin and the hair.

Besides the above essential components, other components conventionally used in the detergent composition for the skin and the hair may optionally be added to the composition of the present invention. Such optional components, which can be incorporated in the composition of the present invention in an amount not to impair its intended effects, include alcohol (e.g. ethanol), viscosity modifier or conditioning agents (e.g. anionic, nonionic, or cationic polymers), moisturizing agents (e.g. glycerol, sorbitole), organic or inorganic powders exhibiting scrubbings effects, preservatives, UV absorbers, antiseptics, perfumes, pigments, and the like.

The detergent composition of the present invention can be prepared according to a conventional method into products of any optional form, including solid, paste, liquid, and the like. It can be served as a detergent for washing the hair, skin, clothes, tableware, dishes, and the like, with especially preferable application being face cleansers, shampoos, body shampoos, etc. for washing the hair and skin.

Other features of the invention will become apparent in the course of the following description of the exemplary embodiments which are given for illustration of the invention and are not intended to be limiting thereof.

EXAMPLES

Synthetic Example 1

To a 5 liter four necked flask equipped with a thermometer, a dropping funnel, and a stirrer, replaced with dry nitrogen gas, were charged at room temperature acetonitrile (300 ml) and methyltosylate (93.10 gm; 0.500 mol), and the mixture was stirred while increasing the temperature of the system in an oil bath. 2-Heptyl-2-oxazoline (375 gm; 2.215 mol) was dropped over 2 hours under refluxing. The polymerization was effected under further refluxing for 24 hours (first step).

A mixture of 2-methyl-2-oxazoline (876.5 gm; 10.30 mol) and acetonitrile (800 ml) was dropped over 2 hours under refluxing. The polymerization was further effected under refluxing for 24 hours (second step).

After cooling, the polymer was precipitated using 20 l of isopropyl ether and dried at 80° C. under vacuum for 48 hours. The monomer composition of the block copolymer thus obtained was measured by the protone-NMR (solvent: heavy hydrogen-chloroform), and the molecular weight was measured by a vapor pressure osmometer (solvent: chloroform). The results are presented in Table 1.

Synthetic Example 2

The polymerization was carried out in the same reaction vessel and under the same conditions as in Synthetic Example 1, by using methyltosylate (119.2 gm; 0.64 mol), 2-heptyl-2-oxazoline (640 gm; 3.78 mol), and acetonitrile (400 ml) in the first step and a mixture of 2-methyl-2-oxazoline (960 gm; 11.3 mol) and acetonitrile (500 ml) in the second step.

The monomer composition and the molecular weight of the block copolymer were measured in the same manner as in Synthetic Example 1. The results are presented in Table 1.

Synthetic Example 3

The polymerization was carried out in the same reaction vessel and under the same conditions as in Synthetic Example 1 by using methyltosylate (92.56 gm; 0.50 mol), 2-ethyl-2-oxazoline (870.0 gm; 8.78 mol), and acetonitrile (500 ml) in the first step and a mixture of 2-undecyl-2-oxazoline (373.2 gm; 1.66 mol) and acetonitrile (100 ml) in the second step.

The monomer composition and the molecular weight of the block copolymer were measured in the same manner as in Synthetic Example 1. The results are presented in Table 1.

Synthetic Example 4

The polymerization was carried out in the same reaction vessel and under the same conditions as in Synthetic Example 1 by using methyltosylate (186.2 gm; 1.00 mol), 2-phenyl-2-oxazoline (500.0 gm; 3.28 mol), and acetonitrile (300 ml) in the first step and a mixture of 2-ethyl-2-oxazoline (500 gm; 5.05 mol) and acetonitrile (600 ml) in the second step.

The monomer composition and the molecular weight of the block copolymer were measured in the same manner as in Synthetic Example 1. The results are presented in Table 1.

TABLE 1

| Synthetic Example | $\left[\begin{array}{c}-N-CH_2-CH_2-\\ \|\\ R'-C=O\end{array}\right]_m$ R' | $\left[\begin{array}{c}-N-CH_2-CH_2-\\ \|\\ R''-C=O\end{array}\right]_n$ R'' | Ratio of $\left[\begin{array}{c}-N-CH_2-CH_2-\\ \|\\ R'-C=O\end{array}\right]_m : \left[\begin{array}{c}-N-CH_2-CH_2-\\ \|\\ R''-C=O\end{array}\right]_n$ Determined by Protone-NMR | Number Average Molecular Weight Determined by Osmometer |
|---|---|---|---|---|
| 1 | $C_7H_{15}$ | $CH_3$ | 29.8/70.2 | 2480 |
| 2 | $C_7H_{15}$ | $CH_3$ | 41.2/58.8 | 2530 |
| 3 | $C_2H_5$ | $C_{11}H_{23}$ | 72.0/28.0 | 2670 |
| 4 | Phenyl | $C_2H_5$ | 48.2/51.8 | 980 |

Synthetic Examples 5-9

Block polymers of $-(I-2)_m-(I-1)_n-$ type shown in Table 2 were prepared in the same manner as in Synthetic Examples 1.

TABLE 2

| Synthetic Example | $R^1$ in (I-1) | $R^2$ in (I-2) | Ratio by weight $(I-1)_n/(I-2)_m$ | Average Molecular Weight |
|---|---|---|---|---|
| 5 | Methyl | Heptyl | 70/30 | 613 |
| 6 | Methyl | Heptyl | 70/30 | 2500 |
| 7 | Methyl | Heptyl | 50/50 | 2500 |
| 8 | Methyl | Heptyl | 60/40 | 4000 |
| 9 | Methyl | Undecyl | 70/30 | 2000 |

Synthetic Examples 10-11

Block copolymers of $-(I-2)_{m'}-(I-1)_n-(I-2)_{m''}$ type shown in Table 3 were prepared in the same manner as in Synthetic Examples 1.

TABLE 3

| Synthetic Example | $R^1$ in (I-1) | $R^2$ in (I-2) | Ratio by weight $(I-1)_n/[(I-2)_{m'} + (I-2)_{m''}]$ | Average Molecular Weight |
|---|---|---|---|---|
| 10 | Methyl | Heptyl | 70/30 | 2500 |
| 11 | Methyl | Undecyl | 70/30 | 2500 |

Synthetic Examples 12-13

Random Copolymers shown in Table 4 were prepared in one step by mixing two types of monomers according to the procedures of in Synthetic Examples 1.

TABLE 4

| Synthetic Example | $R^1$ in (I-1) | $R^2$ in (I-2) | Ratio by weight $(I-1)/(I-2)$ | Average Molecular Weight |
|---|---|---|---|---|
| 12 | Methyl | Heptyl | 70/30 | 2500 |
| 13 | Methyl | Undecyl | 70/30 | 2000 |

Test Example 1

Each polymer prepared in Synthetic Examples 1-4 was dissolved in water to a concentration of 1%. The water-solubility (cloud point), surface tension, foam stability, solubilizing ability, irritation to the skin were evaluated on the solutions using poloxyethylene(30) lauryl ether as a control. The results are shown in Table 5.

TABLE 5

| Tested Polymer Prepared in Synthetic Example | Cloud point | Surface Tension (dyne/cm) *1 | Foam Stability (%) *2 | Solubilizing Ability *3 | Irritation to the skin *4 |
|---|---|---|---|---|---|
| 1 | 100° C. + | 28.0 | 95 | 100 | 0.5 |
| 2 | 100° C. + | 27.2 | 93 | 150 | 0.5 |
| 3 | 100° C. + | 32.5 | 93 | 125 | 0.5 |
| 4 | 100° C. + | 35.2 | 90 | 80 | 0.8 |
| Poloxyethylene (30) lauryl ether | 100° C. + | 38.0 | 20 | 50 | 1.0 |

*1 Surface tension: Whilhelmy method, 30° C.

*2 Foam stability: $\dfrac{\text{Volume of foam 5 minutes after stirring is terminated}}{\text{Volume of foam 10 minutes after stirring is terminated}} \times 100$

*3 Solubilizing ability:
Relative value taking the amount of Sudan III dissolved in the polymer solution of Synthetic Example 1 as 100. The amount dissolved in the solution was determined by the absorption at 500 nm.

*4 Irritation to the skin:
Each solution (8 ml) was subjected to continuous washing by ten women and, after 24 hours, the washing site (left side of the forearm) was observed by the naked eye.
The roughening of the skin was determined by the following standard.

No roughening of the skin was observed: 0
Slight roughening of the skin was observed: 1
Roughening of the skin was observed: 2

TABLE 5-continued

| | |
|---|---|
| Roughening of the skin was rather serious: | 3 |
| Serious roughening of the skin was observed: | 4 |

Test Example 2

Polymers prepared in Synthetic Examples 5-13 were dissolved in water to a concentration of 1%. The surface tension, foam stability, and solubilizing ability were compared on the solutions. The results are shown in Table 6.

TABLE 6

| Tested Polymer Prepared in Synthetic Example | Surface Tension (dyne/cm) | Foam Stacy (%) | Solubilizing Ability * |
|---|---|---|---|
| 5 | 35.0 | 94 | 100 |
| 6 | 32.0 | 93 | 180 |
| 7 | 29.0 | 94 | 450 |
| 8 | 29.0 | 87 | 450 |
| 9 | 40.0 | 82 | 200 |
| 10 | 30.0 | 92 | 160 |
| 11 | 40.0 | 90 | 200 |
| 12 | 29.0 | 94 | 140 |
| 13 | 40.0 | 81 | 200 |
| Poloxyethylene (30) lauryl ether | 38.0 | 20 | 50 |

* Relative value

EXAMPLE 1

Detergent compositions shown in Table 7 were prepared to evaluate the freshness after washing and the irritation after washing (face was washed 3 times a day for one week, each time for one minute, in warm water; unusual feelings e.g. dryness, etc. were questioned). The results are shown in Table 7.

Evaluation Standard

Freshness:
 AAA: Very good
 BBB: Good
 CCC: Normal
 DDD: Bad
Irritation:
 AAA: No irritation was felt
 BBB: Irritation was hardly felt
 CCC: Irritation was slightly felt
 DDD: Irritation was felt

TABLE 7

| Component | Invention Composition 1 | 2 | 3 | 4 | Comparative Composition 1 | 2 |
|---|---|---|---|---|---|---|
| Sodium laurate | 10 | 5 | — | — | 20 | — |
| Triethanolamine laurate | — | — | 10 | 5 | — | 20 |
| Polymer (A) * | 10 | 15 | 10 | 15 | — | — |
| Propylene glycol | 5 | 5 | 5 | 5 | 5 | 5 |
| Ethanol | 5 | 5 | 5 | 5 | 5 | 5 |
| Purified water | Balance | | | | | |
| Freshness | AAA | AAA | AAA | AAA | DDD | DDD |
| Irritation | BBB | AAA | AAA | AAA | DDD | CCC |

* The polymer prepared in Synthetic Example 1.

As demonstrated in Table 7, the detergent compositions of the present invention were excellent in the feeling after use and imparted no irritative feeling. All tested compositions of the present invention had good foam-breaking property. The same good results were obtained by using the polymers prepared in Synthetic Examples 2-13 instead of that of Synthetic Example 1.

| | % by weight |
|---|---|
| Example 2 Liquid Face Cleanser: | |
| Polymer (A) * | 10 |
| Sodium monolaurate | 35 |
| Sodium lauroyl sarcosine | 7 |
| Polyethylene glycol (M.W. 10,000) | 5 |
| Propylene glycol | 5 |
| Perfume | q.s. |
| Water | Balance |
| Total | 100 |

* The polymer prepared in Synthetic Example 1.

| | % by weight |
|---|---|
| Example 3 Antidundraff Shampoo: | |
| Polymer (A) * | 8 |
| Sodium N-lauroylglutamate | 10 |
| Octopyrrox | 1 |
| Ethyl alcohol | 2 |
| Perfume. Pigment | q.s. |
| Water | Balance |
| Total | 100 |

* The polymer prepared in Synthetic Example 1.

The antidandruff shampoo exhibited extremely low irritation to the skin and excellent antidandruff effects.

| | % by weight |
|---|---|
| Example 4 Light Detergent Composition: | |
| Polymer (A) * | 15 |
| Triethanolamine monolaurate | 10 |
| Ethyl alcohol | 8 |
| Perfume | q.s. |
| Water | Balance |
| Total | 100 |

* The polymer prepared in Synthetic Example 1.

The light detergent exhibited extremely low irritation to the skin and excellent detergency.

| | % by weight |
|---|---|
| Example 5 Bath Room Detergent Composition: | |
| Polymer (A) * | 4 |
| Sodium lauryl ether sulfate | 4 |
| Citric acid | 0.7 |
| Water | Balance |
| Total | 100 |

* The polymer prepared in Synthetic Example 1.

The light detergent composition exhibited excellent detergency, effectively removing soap sludge attached to the bath tab.

EXAMPLE 6

Detergent compositions shown in Table 8 were prepared to evaluate their foaming capability and the quality of the foam. The results are shown in Table 8, in which the following standard applies regarding to the evaluation.
 AAA: Very good
 BBB: Good CCC: Not good
DDD: Bad

TABLE 8

| Component (wt. %) | Invention Composition | | Comparative Composition |
|---|---|---|---|
| | 5 | 6 | 3 |
| Polyoxiethylene(20) stearyl ether | 5 | 10 | 20 |
| Polymer (A) * | 15 | 10 | 0 |
| Polyethylene glycol (M.W. 10,000) | 5 | 5 | 5 |
| Ethanol | 5 | 5 | 5 |
| Purified water | 70 | 70 | 70 |
| <Evaluation> | | | |
| Foaming capability | BBB | BBB | DDD |
| Quality of the foam | BBB | AAA | CCC |

* The polymer prepared in Synthetic Example 1.

The results shown in Table 8 demonstrate that the combined use of a nonionic surface active agent and polymer (A) of the present invention promoted both the forming capability and the quality of the foam. Improvements in the detergency was also confirmed. The same results were obtained by replacing the polymer prepared in Synthetic Example 1 with those prepared in Synthetic Examples 2-13.

EXAMPLE 7

Detergent compositions shown in Table 9 were prepared to evaluate their foaming capability, detergency, the sensation which the washed clothes provided to the skin. The results are shown in Table 9, in which the same standard of evaluation applies with respect to the foaming capability and the detergency. The following standard applies with respect to the evaluation of the sensation washed chlothes.

AAA: Not sticky
BBB: Slightly sticky
CCC: Sticky

TABLE 9

| Component (wt. %) | Invention Composition | | Comparative Composition |
|---|---|---|---|
| | 7 | 8 | 4 |
| Alkylglycoside *1 | 3 | 15 | 20 |
| Polymer (A) *2 | 15 | 5 | 0 |
| Polyethylene glycol (M.W. 10,000) | 5 | 5 | 5 |
| Ethanol | 5 | 5 | 5 |
| Purified water | 70 | 70 | 70 |
| <Evaluation> | | | |
| Foaming capability | AAA | BBB | CCC |
| Sensation of washed chlothes | AAA | AAA | CCC |

*2 The polymer prepared in Synthetic Example 1.
*1 Average carbon atoms in the alkyl group: 11
Average glucose polymerization degree: 1.3

The Table 9 shows that the detergent composition of the present invention to which the polymer (A) is used together with an alkylglycoside greatly improved the foaming capability, detergency, and the sensation which the washed chlothes provide as compared with the composition in which the alkylglycoside was used alone. All detergent compositions were confirmed to exhibit good detergency.

| | % by weight |
|---|---|
| Example 8 Liquid Face Cleanser: | |
| Polymer (A) * | 15 |
| Alkylglycoside ** | 15 |
| Triethanolamine laurate | 10 |
| Plyethylene glycol (M.W. 10,000) | 5 |
| Water | 55 |
| Total | 100 |

* The polymer prepared in Synthetic Example 1.
** Average carbon atoms in the alkyl group: 11
Average glucose polymerization degree: 1.3

| Example 9 Body Cleanser: | |
|---|---|
| Polymer (A) * | 15 |
| Polyoxyethylene(20) stearyl ether | 15 |
| Sodium lauroyl sarcosine | 10 |
| Plyethylene glycol (M.W. 10,000) | 5 |
| Water | 55 |
| Total | 100 |

* The polymer prepared in Synthetic Example 2.

| Example 10 Antidundraff Shampoo: | |
|---|---|
| Polymer (A) * | 8 |
| Laurylmonoglycoside | 10 |
| Octopyrrox | 1 |
| Ethyl alcohol | 2 |
| Perfume, Pigment | q.s. |
| Water | Balance |
| Total | 100 |

* The polymer prepared in Synthetic Example 1.

The antidandruff shampoo exhibited extremely low irritation to the skin and excellent antidandruff effects.

| | % by weight |
|---|---|
| Example 11 Light Detergent Composition: | |
| Polymer (A) * | 8 |
| Laurylpolyglycoside (Glucose polymerization degree 1.4) | 10 |
| Ethyl alcohol | 8 |
| Perfume | q.s. |
| Water | Balance |
| Total | 100 |

* The polymer prepared in Synthetic Example 1.

The light detergent exhibited extremely low irritation to the skin and excellent detergency.

| | % by weight |
|---|---|
| Example 12 Bath Room Detergent Composition: | |
| Polymer (A) * | 4 |
| Decylmonoglycoside | 4 |
| Citric acid | 0.7 |
| Water | Balance |
| Total | 100 |

* The polymer prepared in Synthetic Example 1.

The light detergent composition exhibited excellent detergency, effectively removing soap sludge attached to the bath tab.

EXAMPLE 13

Detergent compositions shown in Table 10 were prepared to evaluate the quality of the foam and detergency. The results are shown in Table 10, in which the following evaluation standard applies.

Quality of the foam:
AAA: Very fine
BBB: Fine
CCC: Slightly rough

Detergency:
  AAA: Very good
  BBB: Good
  CCC: Normal

TABLE 10

| Component (wt. %) | Invention Composition 9 | Invention Composition 10 | Comparative Composition 5 |
| --- | --- | --- | --- |
| Lauryldimethylamino acetic acid betaine | 10 | 5 | 20 |
| Polymer (A) * | 10 | 15 | 0 |
| Polyethylene glycol | 5 | 5 | 5 |
| Ethanol | 5 | 5 | 5 |
| Purified water | 70 | 70 | 70 |
| <Evaluation> | | | |
| Quality of the foam | AAA | AAA | CCC |
| Detergency | AAA | BBB | CCC |

*2 The polymer prepared in Synthetic Example 1.

As evident from Table 10, the detergent composition of the present invention produced fine foam and exhibited excellent detergency. The same results were obtained by replacing the polymer prepared in Synthetic Example 1 with those prepared in Synthetic Examples 2-13. All composition of the present invention gave a good feeling after washing.

| | % by weight |
| --- | --- |
| Example 14 Liquid Face Cleanser: | |
| Polymer (A) * | 10 |
| Lauryldimethylamine oxide | 15 |
| Sodium Lauroyl sarcosine | 5 |
| Water | Balance |
| Total | 100 |

* The polymer prepared in Synthetic Example 1.

| Example 15 Antidundraff Shampoo: | |
| --- | --- |
| Polymer (A) * | 8 |
| Lauryldimethylamino acetic acid betaine | 8 |
| Octopyrrox | 1 |
| Ethyl alcohol | 2 |
| Perfume, Pigment | q.s. |
| Water | Balance |
| Total | 100 |

* The polymer prepared in Synthetic Example 1.

The antidandruff shampoo exhibited extremely low irritation to the skin and excellent antidandruff effects.

| | % by weight |
| --- | --- |
| Example 16 Light Detergent Composition: | |
| Polymer (A) * | 8 |
| Compound of formula (XVI) ($R^{35}$ = coconut oil fatty acid residue) | 10 |
| Ethyl alcohol | 8 |
| Perfume | q.s. |
| Water | Balance |
| Total | 100 |

* The polymer prepared in Synthetic Example 1.

The light detergent exhibited extremely low irritation to the skin and excellent detergency.

| | % by weight |
| --- | --- |
| Example 17 Bath Room Detergent Composition: | |
| Polymer (A) * | 4 |
| Lauryldimethylamine oxide | 4 |
| Citric acid | 0.7 |
| Water | Balance |
| Total | 100 |

* The polymer prepared in Synthetic Example 1.

The light detergent composition exhibited excellent detergency, effectively removing soap sludge attached to the bath tab.

EXAMPLE 18

Skin detergent compositions listed in Table 11 were prepared according to a conventional method to evaluate the quality of the foam and the slippery feeling while rinsing. The results are shown in Table 11, in which the following evaluation standard applies.

Quality of the foam:
  AAA:
  BBB: Fine
  CCC: Normal
  DDD: Rough

Slipperiness while rinsing:
  AAA: No slipperiness was felt
  BBB: Slipperiness was hardly felt
  CCC: Slipperiness was felt
  DDD: Slipperiness was significant

TABLE 11

| Component (wt. %) | Invention Composition 11 | Invention Composition 12 | Comparative Composition 6 |
| --- | --- | --- | --- |
| Polymer (A) * | 10 | 15 | 0 |
| Octadecyldimethylbenzyl chloride | 9 | 4.5 | 18 |
| Dodecyltrimethyl ammonium chloride | 1 | 0.5 | 2 |
| Ethanol | 3 | 3 | 3 |
| Glycerine | 4 | 4 | 4 |
| Purified water | Balance | Balance | Balance |
| <Evaluation> | | | |
| Quality of the foam | AAA | AAA | CCC |
| Slipperiness | BBB | BBB | CCC |

*2 The polymer prepared in Synthetic Example 1.

As evident from Table 11, the skin detergent composition of the present invention produced fine foam and imparted very low slippery feeling, and yet exhibited very excellent detergency. In addition, no irritation to the skin was felt over a period of repeated sue. The same results were obtained by replacing the polymer prepared in Synthetic Example 1 with those prepared in Synthetic Examples 2-13. All composition of the present invention gave a good feeling after washing.

EXAMPLE 19

Skin detergent compositions listed in Table 12 were prepared in the same manner as in Example 18 to evaluate the quality of the foam and the slippery feeling after use. The results are shown in Table 12, in which the same evaluation standard as in Example 18 applies

TABLE 12

| Component (wt. %) | Invention Composition 13 | Invention Composition 14 | Comparative Composition 7 |
| --- | --- | --- | --- |
| Octadecyltrimethyl-ammonium chloride | 10 | 5 | 20 |
| Polymer (A) * | 10 | 15 | 0 |
| Glycerine | 4 | 4 | 4 |
| Ethanol | 3 | 3 | 3 |
| Purified water | Balance | Balance | Balance |

TABLE 12-continued

| Component (wt. %) | Invention Composition 13 | Invention Composition 14 | Comparative Composition 7 |
|---|---|---|---|
| <Evaluation> | | | |
| Quality of the foam | AAA | AAA | CCC |
| Slipperiness | BBB | BBB | CCC |

*2 The polymer prepared in Synthetic Example 2.

As evident from Table 12, the skin detergent composition of the present invention produced fine foam and imparted very low slippery feeling, and yet exhibited very excellent detergency. In addition, no irritation to the skin was felt over a period of repeated use. The same results were obtained by replacing the polymer prepared in Synthetic Example 2 with those prepared in Synthetic Examples 1 and 3-13. All composition of the present invention gave a good feeling after washing.

| | % by weight |
|---|---|
| Example 20 Liquid Face Cleanser: | |
| Polymer (A) * | 12 |
| Dodecyldimethylbenzyl-ammonium chloride | 24 |
| Polyoxyethylene(20) stearyl ether | 10 |
| Perfume | q.s. |
| Water | Balance |
| Total | 100 |

* The polymer prepared in Synthetic Example 1.

The above liquid face cleanser exhibited only very weak irritation to the skin, producing foam with excellent quality. It provided a good feeling after use. The detergency was also excellent.

| | % by weight |
|---|---|
| Example 21 Antidundraff Shampoo: | |
| Polymer (A) * | 12 |
| Docosyltrimethylammonium chloride | 0.5 |
| Octopyrrox | 1 |
| Ethyl alcohol | 2 |
| Perfume, Pigment | q.s. |
| Water | Balance |

* The polymer prepared in Synthetic Example 1.

The antidandruff shampoo exhibited extremely low irritation to the skin and excellent antidandruff effects.

| | % by weight |
|---|---|
| Example 22 Shampoo: | |
| Polymer (A) * | 15 |
| 2-Dodecylhexadecyltrimethyl ammonium chloride | 2 |
| Cetostearyl alcohol | 3 |
| Propylene glycol | 3 |
| Water | Balance |
| Total | 100 |

* The polymer prepared in Synthetic Example 1.

The shampoo exhibited extremely low irritation to the skin and excellent foaming capability.

Obviously, numerous modifications and variations of the present invention are possible in light of the above teachings. It is therefore to be understood that within the scope of the appended claims, the invention may be practiced otherwise than as specifically described herein.

What is claimed is:
1. A detergent composition comprising:
(A) a polymeric compound comprising recurring units (I-1) and I-2) at a ratio by weight of 9:1-1:9,

wherein $R^1$ is a hydrogen or a methyl or ethyl group, $R^2$ represents an alkyl, aryl or aralkyl group having 4-15 carbon atoms, and
(B) at least one different compound selected from the group consisting of monomeric anionic surface active agents, monomeric nonionic surface active agents, monomeric amphoteric surface active agents, monomeric cationic surface active agents, wherein the weight ratio of component (A) to component (B) is form 5/1 to 1/5.

2. The detergent composition according to claim 1, wherein the component (B) is an anionic surface active agent.

3. The detergent composition according to claim 1, wherein the component (B) is a nonionic surface active agent.

4. The detergent composition according to claim 1, wherein the component (B) is an amphoteric surface active agent.

5. The detergent composition according to claim 1, wherein the component (B) is a cationic surface active agent.

6. The detergent composition according to claim 2, wherein the component (B) is at least one anionic surface active agent selected from the group consisting of fatty acid, alkylsulfate, alkyl ether carboxylate, polyoxyethylenealkyl ether sulfate, phosphate, N-acylamino acid, isethionate, and sulfo-succinate anionic surface active agents.

7. The detergent composition according to claim 3, wherein the component (B) is at least one nonionic surface active agent selected from the group consisting of polyoxyalkylene, saccharide ester, saccharide ether, saccharide amide, polyglycerine fatty acid ester, polyglycerine alkyl ether, and alkylamine oxide nonionic surface active agents.

8. The detergent composition according to claim 4, wherein the component (B) is at least one amphoteric surface active agent selected from the group consisting of amidoamine, amino acid, betaine, sulfate, sulfonate, phosphate, and amine oxide amphoteric surface active agents.

9. The detergent composition according to claim 5, wherein the component (B) is at least one cationic surface active agent selected from the group consisting of amine salt, polyoxyethylene alkylamine, long chain quaternary ammonium salt, and cyclic quaternary ammonium salt cationic surface active agents.

10. The detergent composition according to claim 1, wherein the component (A) is a copolymer having an average molecular weight of 500-20,000.

11. The detergent composition according to claim 1, wherein the component (A) is a copolymer containing the recurring units (I-1) and (I-2) at a ratio by weight of 9:1–4:6.

12. The detergent composition according to claim 2, wherein the component (B) is sodium laurate or triethanolamine laurate.

13. The detergent composition according to claim 3, wherein the component (B) is polyoxyethylene stearyl ether or an alkylglycoside.

14. The detergent composition according to claim 4, wherein the component (B) is lauryldimethylamino acetic acid betaine.

15. The detergent composition according to claim 5, wherein the component (B) is a mixture of octadecyldimethylbenzyl chloride and dodecyltrimethyl ammonium-chloride.

16. The detergent composition according to claim 5, wherein the component (B) is octadecyltrimethyl ammonium chloride.

* * * * *

UNITED STATES PATENT AND TRADEMARK OFFICE
CERTIFICATE OF CORRECTION

PATENT NO. : 5,183,601

DATED : FEBRUARY 2, 1993

INVENTOR(S) : YASUHIRO JISAI ET AL

It is certified that error appears in the above-identified patent and that said Letters Patent is hereby corrected as shown below:

Column 3, line 9, "sulfosuccinate" should read --sulfo-succinate--.

Column 7, line 50, "$\geq CH_2CH_2COOM^2$" should read -- $-CH_2CH_2COOM^2$--.

Column 8, line 65, "of" should read --or--.

Column 9, line 9, after "$R^{26}$", insert --,--.

Column 12, line 41 "by weight" should be in the same paragraph.

Column 13, line 47, after "5:0.1-1:5", insert --.--.

Column 18, line 23, "Antidundraff" should read --Antidandruff--;
line 59, "tab" should read --tub--.

UNITED STATES PATENT AND TRADEMARK OFFICE
CERTIFICATE OF CORRECTION

PATENT NO. : 5,183,601
DATED : FEBRUARY 2, 1993
INVENTOR(S) : YASUHIRO JISAI ET AL

It is certified that error appears in the above-identified patent and that said Letters Patent is hereby corrected as shown below:

```
Column 19, line 35, "chlothes" should read --clothes--;
           line 60, "chlothes" should read --clothes--.

Column 20, line 20, "Antidundraff" should read --Antidandruff--;
           line 58, "tab" should be --tub--.

Column 21, line 35, "Antidundraff" should read --Antidandruff--.

Column 22, line 9, "tab" should read --tub--;
           line 18, "AAA:" should read --AAA:  Very Fine--;
           line 47, "sue" should read --use--;
           line 59, after "applies", insert --.--.

Column 23, line 40, "Antidundraff" should read --Antidandruff--.

Column 24, Claim 1, line 6, "I-2)" should read --(I-2)--;
                    line 23, "agents, monomeric" should read
      --agents and monomeric--;
                    line 24, "form" should read --from--.
```

Signed and Sealed this

Twenty-third Day of August, 1994

Attest:

BRUCE LEHMAN

Attesting Officer

Commissioner of Patents and Trademarks